United States Patent
Lee et al.

(10) Patent No.: US 10,253,317 B2
(45) Date of Patent: Apr. 9, 2019

(54) DNA-RNA HYBRID PARTICLES AND MANUFACTURING METHOD THEREOF

(71) Applicant: UNIVERSITY OF SEOUL INDUSTRY COOPERATION FOUNDATION, Seoul (KR)

(72) Inventors: Jong-Bum Lee, Seoul (KR); Yong-Kuk Park, Seoul (KR)

(73) Assignee: UNIVERSITY OF SEOUL INDUSTRY COOPERATION FOUNDATION, Seoul (KR)

( * ) Notice: Subject to any disclaimer, the term of this patent is extended or adjusted under 35 U.S.C. 154(b) by 49 days.

(21) Appl. No.: 15/321,748

(22) PCT Filed: Jun. 30, 2015

(86) PCT No.: PCT/KR2015/006707
§ 371 (c)(1),
(2) Date: Apr. 24, 2017

(87) PCT Pub. No.: WO2016/003162
PCT Pub. Date: Jan. 7, 2016

(65) Prior Publication Data
US 2017/0240889 A1     Aug. 24, 2017

(30) Foreign Application Priority Data
Jun. 30, 2014 (KR) .................. 10-2014-0080448

(51) Int. Cl.
| | |
|---|---|
| *C12N 15/113* | (2010.01) |
| *C12N 15/64* | (2006.01) |
| *C12P 19/34* | (2006.01) |
| *C12Q 1/6844* | (2018.01) |
| *C12Q 1/6853* | (2018.01) |
| *C12Q 1/6867* | (2018.01) |

(52) U.S. Cl.
CPC ............ *C12N 15/113* (2013.01); *C12P 19/34* (2013.01); *C12Q 1/6844* (2013.01); *C12Q 1/6853* (2013.01); *C12Q 1/6867* (2013.01); *C12N 2310/14* (2013.01); *C12N 2310/16* (2013.01); *C12N 2310/532* (2013.01); *C12N 2320/32* (2013.01)

(58) Field of Classification Search
CPC ............... C12Q 1/6867; C12Q 1/6844; C12Q 2525/205; C12Q 2525/207; C12Q 2525/307; C12N 2310/16; C12N 2310/532
USPC ................... 435/6.1, 6.11, 6.12, 91.1, 91.31; 536/23.1, 24.5
See application file for complete search history.

(56) References Cited

FOREIGN PATENT DOCUMENTS

| | | |
|---|---|---|
| KR | 10-2005-0057290 A | 6/2005 |
| KR | 10-2007-0061770 A | 6/2007 |

OTHER PUBLICATIONS

Office Action dated Mar. 15, 2016 of Korean Patent Application No. KR-10-2014-0080448, which corresponds to the above referenced application.

*Primary Examiner* — Jane J Zara
(74) *Attorney, Agent, or Firm* — Goldilocks Zone IP Law

(57) ABSTRACT

Disclosed are particles which are introduced into target cells and suppress the expression of specific genes, and a method of manufacturing such particles. More particularly, the present invention relates to DNA-RNA hybrid particles that comprise a DNA strand and an RNA strand that binds to the DNA strand through partial complementary base pairing, in which the DNA strand comprises an aptamer sequence that is able to bind to a target protein produced in a target cell, and the RNA strand comprises an siRNA sequence that binds to a target RNA in the target cell to suppress protein expression from the target RNA. Such hybrid particles are capable of effectively delivering an siRNA therapeutic agent into target cells for the treatment of disease, and have resistance against digestion by in vivo nucleases, DNase and RNase, owing to complementary binding formed between DNA and RNA strands. Also, the present invention relates to a method of manufacturing such DNA-RNA hybrid particles.

7 Claims, 14 Drawing Sheets
(4 of 14 Drawing Sheet(s) Filed in Color)
Specification includes a Sequence Listing.

DNA-RNA HYBRID PARTICLES AND MANUFACTURING METHOD THEREOF

CROSS REFERENCE TO RELATED PATENT APPLICATIONS

This application claims the benefit under 35 U.S.C. Section 371, of PCT International Application No. PCT/KR2015/006707, filed Jun. 30, 2015, which claimed priority to Korean Patent Application No. KR10-2014-0080448, filed Jun. 30, 2014, the disclosures of which are hereby incorporated by the references.

TECHNICAL FIELD

The present invention relates to particles which are introduced into target cells and suppress the expression of specific genes, and a method of manufacturing such particles. More particularly, the present invention relates to DNA-RNA hybrid particles that comprise a DNA strand and an RNA strand that binds to the DNA strand through partial complementary base pairing, in which the DNA strand comprises an aptamer sequence that is able to bind to a target protein produced in a target cell, and the RNA strand comprises an siRNA sequence that binds to a target RNA in the target cell to suppress protein expression from the target RNA. Such hybrid particles are capable of effectively delivering an siRNA therapeutic agent into target cells for the treatment of diseases, are non-toxic in vivo because they are composed of only DNA and RNA molecules, which are biomolecules, thus ensuring safety with no adverse effects, and have resistance against digestion by in vivo nucleases, DNase and RNase, owing to complementary binding formed between DNA and RNA strands. The present invention is also concerned with a method of manufacturing such DNA-RNA hybrid particles.

BACKGROUND ART

Small interfering RNA (siRNA) has been shown to bind to target mRNA and suppress of protein expression from the target mRNA. Due to their effective and sequence-specific gene silencing, siRNA molecules have been highlighted for application as new potential therapeutics. In particular, siRNA-based therapeutics, compared to conventional antisense oligonucleotide-based therapeutics, may exert excellent gene-silencing activity even at low doses and have low cytotoxicity, thus being relatively safe. In order to realize these advantageous effects of siRNA, it is essential that the siRNA is effectively delivered into target cells that express RNA of interest. The siRNA can be delivered, for example, by an organic carrier (polymer) as disclosed in Korean Pat. Publication No. 10-2007-0061770 (published in Jun. 14, 2007) entitled "siRNA-hydrophilic polymer conjugates for intracellular delivery of siRNA and preparation method thereof".

However, conventional carrier systems of siRNA, including the above-mentioned patent publication, still face multiple barriers in delivering siRNA to their target cells, including uptake into cells across the plasma membrane and escape from the endosome into the cytoplasm. Also, the conventional carrier systems have low delivery efficiency since siRNA may be susceptible to nuclease digestion in vivo, and do not ensure safety upon application to humans since organic or inorganic materials are employed as carriers.

DISCLOSURE

Technical Problem

Accordingly, the present invention has been made keeping in mind the above problems encountered in the related art, and it is, therefore, an object of the present invention to provide DNA-RNA hybrid particles that can serve as a therapeutic agent as well as a drug carrier, and a method of manufacturing such hybrid particles.

It is another object of the present invention to provide DNA-RNA hybrid particles capable of safely and effectively delivering an siRNA therapeutic agent into target cells for the treatment of disease, in which a DNA strand binds to an RNA strand through partial complementary base paring to form nano-sized particles having a spherical shape, the DNA strand comprises an aptamer sequence that is able to bind to a target protein, and the RNA strand comprises an siRNA sequence that binds to a target RNA to suppress gene expression. Also, there is provided a method of manufacturing such hybrid particles.

It is a further object of the present invention to provide DNA-RNA hybrid particles that are composed of only DNA and RNA molecules, which are biomolecules, and are thus non-toxic in vivo and ensure safety with no adverse effects. Also, there is provided a method of manufacturing such hybrid particles.

It is yet another object of the present invention to provide DNA-RNA hybrid particles having resistance against digestion by in vivo nucleases, DNase and RNase, through complementary binding famed between DNA and RNA strands, and a method of manufacturing such hybrid particles.

Technical Solution

To accomplish the above described objects, the present invention is implemented in embodiments having the following constructions.

In one embodiment of the present invention, the DNA-RNA hybrid particles according to the present invention comprise a DNA strand and an RNA strand that binds to the DNA strand through partial complementary base pairing, in which the DNA strand comprises an aptamer sequence that is able to bind to a target protein produced in a target cell, and the RNA strand comprises an siRNA sequence that binds to a target RNA in the target cell to suppress protein expression from the target RNA.

In accordance with another embodiment of the present invention, the DNA-RNA hybrid particles according to the present invention are characterized by having a spherical shape.

In accordance with a further embodiment of the present invention, the DNA-RNA hybrid particles according to the present invention are characterized by having a diameter ranging from 100 to 150 nm.

In yet another embodiment of the present invention, the DNA-RNA hybrid particles according to the present invention are formed with DNA and RNA strands that bind and aggregate to each other through partial complementary base pairing.

In still another embodiment of the present invention, the method of manufacturing DNA-RNA hybrid particles according to the present invention comprises the steps of generating a circular DNA template for transcription by allowing complementary base pairing between a primer and a single-stranded DNA (ssDNA) containing a nucleotide sequence complementary to a specific siRNA sequence; generating a circular DNA template for amplification by allowing complementary base pairing between a primer and a single-stranded DNA (ssDNA) containing a nucleotide sequence complementary to a specific aptamer sequence; and performing a stepwise dual enzymatic reaction, by which the circular DNA template for transcription is transcribed using an RNA polymerase to generate an RNA strand containing the siRNA sequence, the circular DNA template for amplification is amplified using a DNA polymerase to generate a DNA strand containing the aptamer sequence, and partial complementary base pairing is allowed to form particles between the RNA strand containing the siRNA sequence and the DNA strand containing the aptamer sequence.

In accordance with still another embodiment of the present invention, the method of manufacturing DNA-RNA hybrid particles according to the present invention is characterized in that the RNA strand containing an siRNA sequence is generated by rolling circle transcription (RCT), and the DNA strand containing an aptamer sequence is generated by rolling circle amplification (RCA).

In accordance with still another embodiment of the present invention, the method of manufacturing DNA-RNA hybrid particles according to the present invention is characterized in that the stepwise dual enzymatic reaction is carried out over a predetermined period of time at activation temperatures for RNA and DNA polymerases, in which the activation temperatures are alternatingly maintained for a reaction time interval.

In accordance with still another embodiment of the present invention, the method of manufacturing DNA-RNA hybrid particles according to the present invention is characterized in that the stepwise dual enzymatic reaction comprises steps of (1) mixing the DNA template for transcription with the RNA polymerase in a container and maintaining an activation temperature for RNA polymerase for a reaction time interval; (2) mixing the DNA template for amplification with the DNA polymerase in an additional container and maintaining an activation temperature for DNA polymerase for a reaction time interval; and (3) mixing the resulting reaction in the container with the resulting reaction in the additional container and alternatingly maintaining the activation temperatures for RNA and DNA polymerases for a reaction time interval over a predetermined period of time.

In accordance with still another embodiment of the present invention, the method of manufacturing DNA-RNA hybrid particles according to the present invention is characterized in that the reaction time interval may be controlled so as to form particles in a predetermined size and shape.

In accordance with still another embodiment of the present invention, the method of manufacturing DNA-RNA hybrid particles according to the present invention is characterized in that the step of generating the circular DNA template for transcription comprises the step of hybridizing a primer and a single-stranded DNA (ssDNA) containing a nucleotide sequence complementary to a specific siRNA sequence through complementary base pairing and the step of ligating a nick in the resulting circular ssDNA with a ligase.

In accordance with still another embodiment of the present invention, the method of manufacturing DNA-RNA hybrid particles according to the present invention is characterized in that the step of generating the circular DNA template for amplification comprises the steps of hybridizing a primer and a single-stranded DNA (ssDNA) containing a nucleotide sequence complementary to a specific aptamer sequence through complementary base pairing and the step of ligating a nick in the resulting circular ssDNA with a ligase.

Advantageous Effects

In accordance with exemplary embodiments of the present invention, the following effects may be obtained.

The present invention may serve as a therapeutic agent as well as a drug carrier.

The present invention is also capable of safely and effectively delivering a therapeutic agent (siRNA) into target cells for the treatment of disease, since a DNA strand binds to an RNA strand through partial complementary base paring to form nano-sized particles in a spherical shape, the DNA strand comprises an aptamer sequence that is able to bind to a target protein, and the RNA strand comprises an siRNA sequence that binds to a target RNA to suppress gene expression.

Further, the present invention is non-toxic in vivo and thus ensures safety with no adverse effects because it is composed of only DNA and RNA molecules, which are biomolecules.

Moreover, the present invention has resistance against digestion by in vivo nucleases, DNase and RNase owing to complementary binding formed between DNA and RNA strands.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
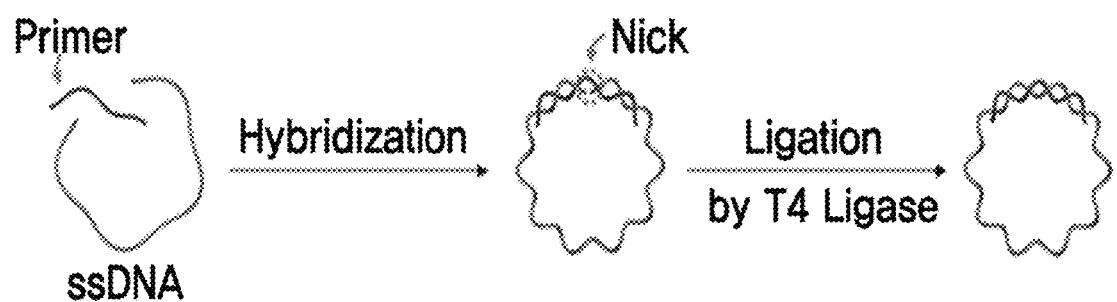
FIG. 1 is a brief view showing the principle of forming a circular DNA template for transcription or amplification.

Hereinafter, a detailed description will be given of DNA-RNA hybrid particles and a manufacturing method thereof according to the present invention, with reference to the appended drawings. Unless otherwise defined, all terms used herein have the same meaning as commonly understood by one of ordinary skill in the art to which the present invention belongs. If the meaning of the team used herein conflicts with the general meaning thereof, it accords to the definition used herein. In the following description of the present invention, detailed descriptions of known constructions and functions incorporated herein will be omitted when they may make the gist of the present invention unclear. As used herein, when any part "comprises" or "contains" any element, it means that other elements are not precluded but may be further included, unless otherwise mentioned.

The present invention is directed to DNA-RNA hybrid particles which are delivered into a target cell and suppress the expression of a target gene. The DNA-RNA hybrid particles comprise a DNA strand and an RNA strand that binds to the DNA strand through partial complementary base pairing. The DNA strand comprises an aptamer sequence that is able to bind to a target protein produced in a target cell, and the RNA strand comprises an siRNA sequence that binds to a target RNA in the target cell to suppress protein expression from the target RNA.

The DNA-RNA hybrid particles have a constant size and shape, and preferably have a spherical shape and a diameter ranging from 100 to 150 nm. The DNA-RNA hybrid particles are formed with DNA and RNA strands that bind and aggregate to each other through partial complementary base pairing.

The DNA strand comprises an aptamer sequence that is able to bind to a target protein produced in a target cell and a nucleotide sequence that binds to the RNA strand through partial complementary base pairing. The RNA strand comprises an siRNA sequence that binds to a target RNA in the target cell to suppress protein expression from the target RNA and a nucleotide sequence that binds to the DNA strand through partial complementary base pairing. The two nucleotide sequences are fully or partially complementary to each other, and the DNA and RNA strands thus bind and aggregate to each other through partial complementary base pairing to form DNA-RNA hybrid particles. The DNA-RNA hybrid particles are effectively delivered into target cells since they have an aptamer sequence capable of binding to a target protein, and their siRNA sequence, which suppresses protein expression from a target RNA, binds to a target RNA, ultimately causing gene silencing (RNA interference). Also, the DNA-RNA hybrid particles are non-toxic in vivo since they are composed of only biomolecules, and have relatively high resistance against digestion by in vivo nucleases, DNase and RNase since they are formed through complementary binding between DNA and RNA strands.

The DNA-RNA hybrid particles will be described in more detail below, and are preferably manufactured according to the method described below without limitation thereto.

The method of manufacturing DNA-RNA hybrid particles comprises the steps of generating a circular DNA template for transcription by allowing complementary base pairing between a primer and a single-stranded DNA (ssDNA) for transcription containing a nucleotide sequence complementary to a specific siRNA sequence; generating a circular DNA template for amplification by allowing complementary base pairing between a primer and a single-stranded DNA (ssDNA) for amplification containing a nucleotide sequence complementary to a specific aptamer sequence; and performing a stepwise dual enzymatic reaction by which the circular DNA template for transcription is transcribed using an RNA polymerase to generate an RNA strand containing the siRNA sequence, the circular DNA template for amplification being amplified using a DNA polymerase to generate a DNA strand containing the aptamer sequence, and partial complementary base pairing being allowed to form particles between the RNA strand containing the siRNA sequence and the DNA strand containing the aptamer sequence.

The step of generating the circular DNA template for transcription, in which complementary base pairing is allowed between a primer and a single-stranded DNA (ssDNA) for transcription to generate a circular DNA template for transcription, comprises the step of hybridizing a primer and a single-stranded DNA (ssDNA) for transcription containing a nucleotide sequence complementary to a specific siRNA sequence through complementary base pairing and the step of ligating a nick in the resulting circular ssDNA with a ligase. The ssDNA for transcription comprises a nucleotide sequence complementary to an siRNA sequence and binding nucleotide sequences allowing partial complementary base pairing with the primer and the ssDNA for amplification. Referring to FIG. 1, the ssDNA for transcription is hybridized with the primer through partial complementary base pairing, and a nick in the resulting circular ssDNA is sealed by a ligase. To the binding nucleotide sequences of the ssDNA for transcription, an amplified DNA strand is bound at the stepwise dual enzymatic reaction step.

The step of generating the circular DNA template for amplification, at which complementary base pairing is allowed between a primer and a single-stranded DNA (ssDNA) for amplification to generate a circular DNA template for amplification, comprises the step of hybridizing a primer and a single-stranded DNA (ssDNA) for amplification containing a nucleotide sequence complementary to a specific aptamer sequence through complementary base pairing and the step of ligating a nick in the resulting circular ssDNA with a ligase. The ssDNA for amplification comprises a nucleotide sequence complementary to an aptamer sequence and binding nucleotide sequences allowing partial complementary base pairing with the primer and the ssDNA for transcription. Referring to FIG. 1, the ssDNA for amplification is hybridized with the primer through partial complementary base pairing, and a nick in the resulting circular ssDNA is sealed by a ligase. To the binding nucleotide sequences of the ssDNA for amplification, a transcribed RNA strand is bound at the stepwise dual enzymatic reaction step.

Figure 2:
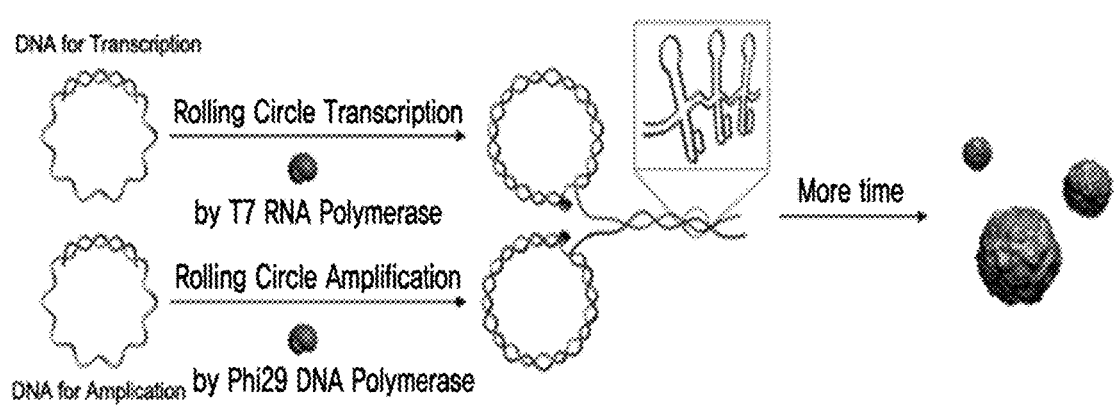
FIG. 2 is a brief view showing the principle of forming hybrid particles using the circular DNA templates for transcription and amplification, respectively.

At the stepwise dual enzymatic reaction, referring to FIG. 2, a long RNA strand is generated from the circular DNA template for transcription by rolling circle transcription (RCT) using an RNA polymerase while a long DNA strand is generated from the circular DNA template for amplification by rolling circle amplification (RCA) using a DNA polymerase, in which the RNA strand, containing an siRNA sequence, binds to the DNA strand, containing an aptamer sequence, through partial complementary base pairing to foam particles. The stepwise dual enzymatic reaction, referring to FIG. 3, comprises the steps of (1) mixing the DNA template for transcription with the RNA polymerase in a container A and maintaining an activation temperature for the RNA polymerase (RPAT) for a reaction time interval; (2) mixing the DNA template for amplification with the DNA polymerase in an additional container B and maintaining an activation temperature for the DNA polymerase (DRAT) for a reaction time interval; and (3) mixing the resulting reaction in the container A with the resulting reaction in the additional container B and alternatingly maintaining the activation temperatures for RNA and DNA polymerases for a reaction time interval over a predetermined period of time. At the stepwise dual enzymatic reaction, because the DNA polymerase may bind to the DNA strand for transcription and thus generate undesired DNA strands, the RCT and RCA reactions are initially performed in different containers for a predetermined reaction time interval in order to increase the polymerization efficiency. At this initial step, each of the two polymerases is allowed to bind to an intended circular DNA strand.

Mode of Invention

A better understanding of the present invention may be obtained through the following examples which are set forth to illustrate, but are not to be construed as the limit of the present invention.

EXAMPLE 1

Preparation of Circular DNA Template for Transcription

1) A single-stranded DNA (ssDNA) for transcription was designed to have binding nucleotide sequences allowing complementary base pairing with a primer and an ssDNA for amplification at its two ends, and a nucleotide sequence complementary to an siRNA sequence (e.g. an anti-luciferase siRNA sequence) between the two end sequences, as follows:

[5'-ATAGTGAGTCGTATTAACGTA (SEQ ID NO: 1)-

CCAACAACTTACGCTGAGTACTTCGATTACTTGAATCGAAGTACTCAGCGTAAGTTT
(SEQ ID NO: 2)-

AGAGGCATATOCCT (SEQ ID NO: 3)-3'].

The primer was designed to have the nucleotide sequence SEQ ID NO: 4 (5'-TAATACGACTCACTATAGGGAT-3').

2) The ssDNA for transcription was mixed with 3 µM of the primer in a tube in a total volume of 100 µl and was subjected to hybridization with the primer in a thermal cycler. During hybridization, the primer was allowed to bind to complementary regions (the binding nucleotide sequences) on both ends of the linear ssDNA, thus yielding the ssDNA in a circular form having a nick therein.

3) Subsequently, a ligation reaction was performed to seal the nick in the circular ssDNA with ligase buffer and T4 ligase, which were added in amounts of ¹⁄₁₀ and ¹⁄₅₀ of the total volume, respectively, at room temperature for 8 hrs.

EXAMPLE 2

Preparation of Circular DNA Template for Amplification

1) A single-stranded DNA (ssDNA) for amplification was designed to have binding nucleotide sequences allowing complementary base pairing with a primer and the ssDNA for transcription at its two ends, and a nucleotide sequence complementary to an aptamer sequence (e.g., a nucleolin (NCL)-aptamer sequence) between the two end sequences, as follows:

[5'-AGGGATATGCCTCTAATAAATATTAA (SEQ ID NO: 5)-

CCACCACCACCACCACAACCACCACCACC (SEQ ID NO: 6)-

AATAATAAGAAGTTGGTACGTTAATACGACTCACTAT (SEQ ID NO: 7)-3'].

The primer was designed to have the nucleotide sequence of SEQ ID NO: 8 (5'-TTAGAGGCATATCCCTATAGTG-3').

2) The ssDNA for amplification was mixed with 3 µM of the primer in a tube in a total volume of 100 µl and was subjected to hybridization with the primer in a thermal cycler. During hybridization, the primer was allowed to bind to complementary regions (the binding nucleotide sequences) on both ends of the linear ssDNA, thus yielding the ssDNA in a circular form having a nick.

3) Subsequently, a ligation reaction was performed to seal the nick in the circular ssDNA with ligase buffer and T4 ligase, which were added in amounts of ¹⁄₁₀ and ¹⁄₅₀ of the total volume, respectively, at room temperature for 8 hrs.

EXAMPLE 3

Preparation of DNA-RNA Hybrid Particles

Figure 3:
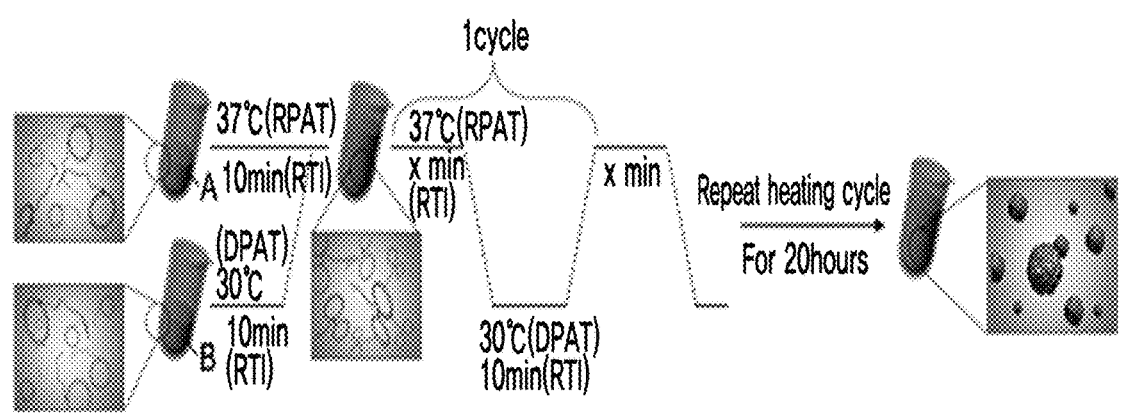
FIG. 3 is a schematic drawing showing a process of forming hybrid particles from the two circular DNA templates for transcription and amplification.

1) As shown in FIG. 3, a rolling circle transcription (RCT) reaction was performed as follows: the closed circular ssDNA for transcription (3 pmol), which was hybridized with the primer, was mixed in a tube A with T7 RNA Polymerase (500 unit), 20 µl of RNAPol Reaction Buffer (40 mM Tris-HCl, 6 mM MgCl$_2$, 10 mM DTT, 2 mM spermidine, pH 7.9 at 25° C.) and rNTP mix (200 nmol) in a total volume of 50 µl, and the mixture was then incubated at an RNA polymerase activation temperature (RPAT) of 37° C. for 10 min (reaction time interval (RTI)).

2) As shown in FIG. 3, a rolling circle amplification (RCA) reaction was performed as follows: the closed circular ssDNA for amplification (3 pmol), which was hybridized with the primer, was mixed in a tube B with Phi29 DNA Polymerase (500 unit), 20 µl of Reaction Buffer (400 mM Tris-HCl, 500 mM KCl, 100 mM MgCl$_2$, 50 mM (NH$_4$)$_2$SO$_4$, 40 mM DTT) and dNTP mix (200 nmol) in a total volume of 50 µl, and the mixture was then incubated at a DNA polymerase activation temperature (DRAT) of 30° C. for 10 min (reaction time interval (RTI)).

3) Thereafter, as shown in FIG. 3, the reaction mixtures of the tubes A and B were mixed and placed in a thermal cycler. The mixture was then subjected to a cycle of RCT at 37° C. for 10 min (RTI) and RCA at 30° C. for 10 min (RTI), and this cycle was repeated for 20 hrs, thus generating DNA-RNA hybrid particles.

EXAMPLE 4

Analysis for the Size and Shape of DNA-RNA Hybrid Particles

Figure 4:
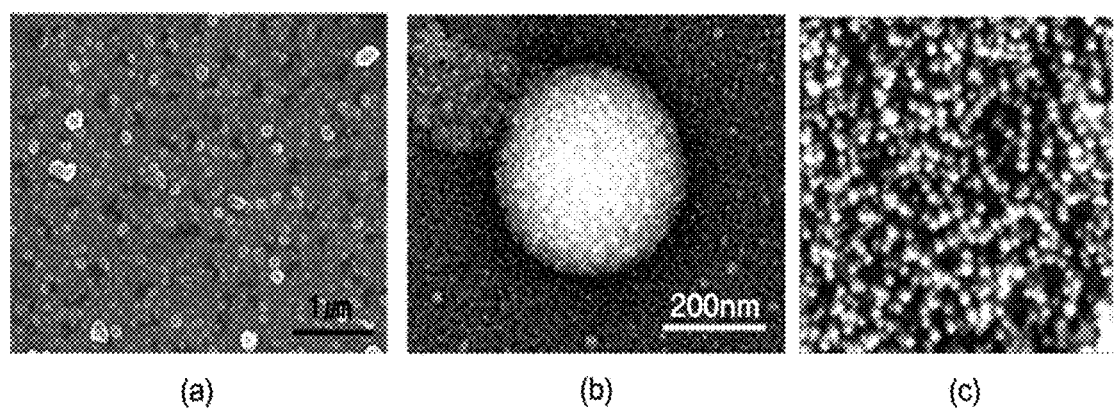
FIG. 4 shows microscopic images of hybrid particles according to an embodiment of the present invention.

The DNA-RNA hybrid particles prepared in Example 3 were analyzed for their size and shape by scanning electron microscopy (SEM), transmission electron microscopy (TEM) and atomic force microscopy (AFM). As shown in the SEM image of FIG. 4(a), the hybrid particles were found to be spherical nano-sized particles having a diameter of 100 to 150 nm. The TEM image of FIG. 4(b) shows that DNA and RNA strands were tightly packed with each other into nano-sized particles. The AFM image of FIG. 4(c) shows particle morphology corresponding to the SEM image.

EXAMPLE 5

Figure 5:
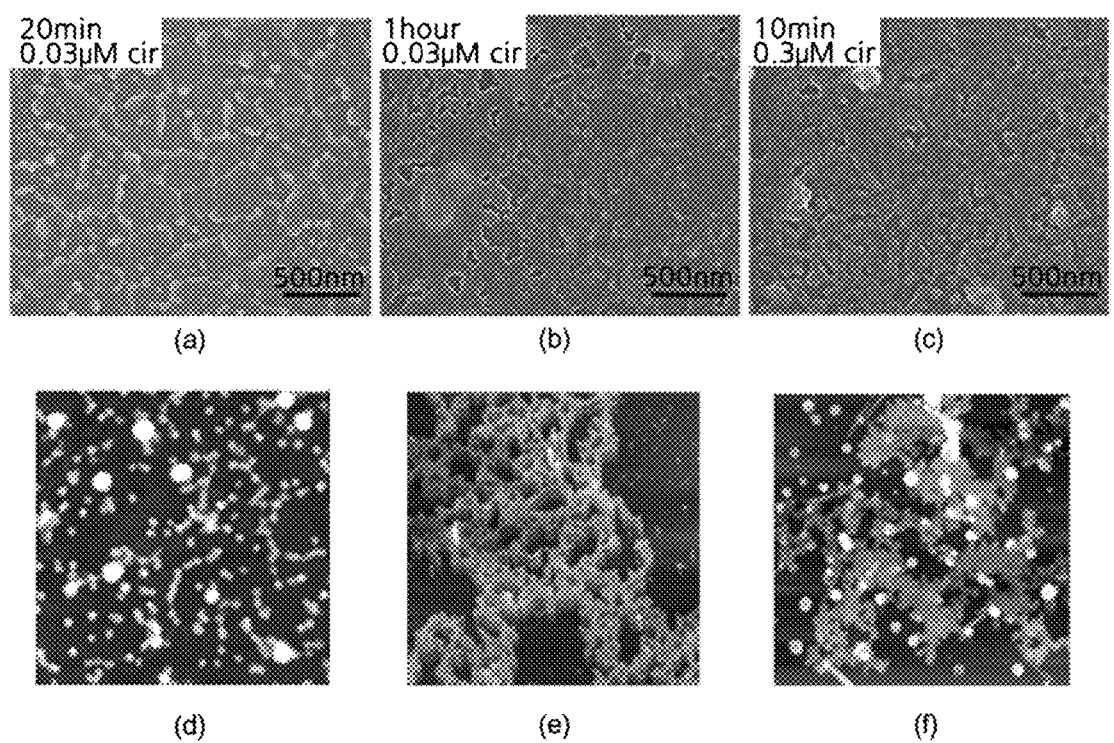
FIG. 5 shows microscopic images of hybrid particles prepared with different reaction time intervals (RTI) or concentrations of circular DNA templates.

Analysis for the Size and Shape of DNA-RNA Hybrid Particles According to Change in RTI and the Concentration of Circular ssDNA 1) DNA-RNA hybrid particles were prepared according to the same procedure as described in Example 3, except that the reaction time interval (RTI) of 10 min was increased to 20 min.
2) DNA-RNA hybrid particles were prepared according to the same procedure as described in Example 3, except that the reaction time interval (RTI) of 10 min was increased to 60 min.
3) DNA-RNA hybrid particles were prepared according to the same procedure as described in Example 3, except that the concentration of each ssDNA for transcription and amplification was increased from 10 pmol up to 30 pmol.
4) The DNA-RNA hybrid particles thus prepared were subjected to scanning electron microscopy (SEM) and atomic force microscopy (And). FIG. 5 shows SEM images of the hybrid particles prepared with the above 1) condition (a), the above 2) condition (b) and the above 3) condition (c). Also, AFM images of the hybrid particles prepared with the above conditions 1), 2) and 3) are given in FIGS. 5(d), (e) and (f), respectively. When the reaction time interval (RTI) was increased to 20 min, both spherical particles and particle aggregations were observed (FIG. 5(a), (d)). The result of extension of RTI up to 60 min was that particles were rarely in a spherical shape but were found to be mostly in an aggregated form (FIG. 5(b), (e)). These results indicate that, as the RTI increases, particles tend to aggregate into a net structure rather than forming a spherical shape. That is believed to be because the turnover frequency between RCA and RCT reactions decreases as the RTI is extended while DNA and RNA strands are synthesized for a longer time in one cycle, thus generating longer DNA and RNA strands in each cycle. These longer DNA and RNA strands may act as threads and become aggregated into a net structure. When the concentration of circular DNA was increased even without change in RTI of 10 min, nanoparticles were found to aggregate into a net structure (FIG. 5(c), (f)).

EXAMPLE 6

Figure 6:
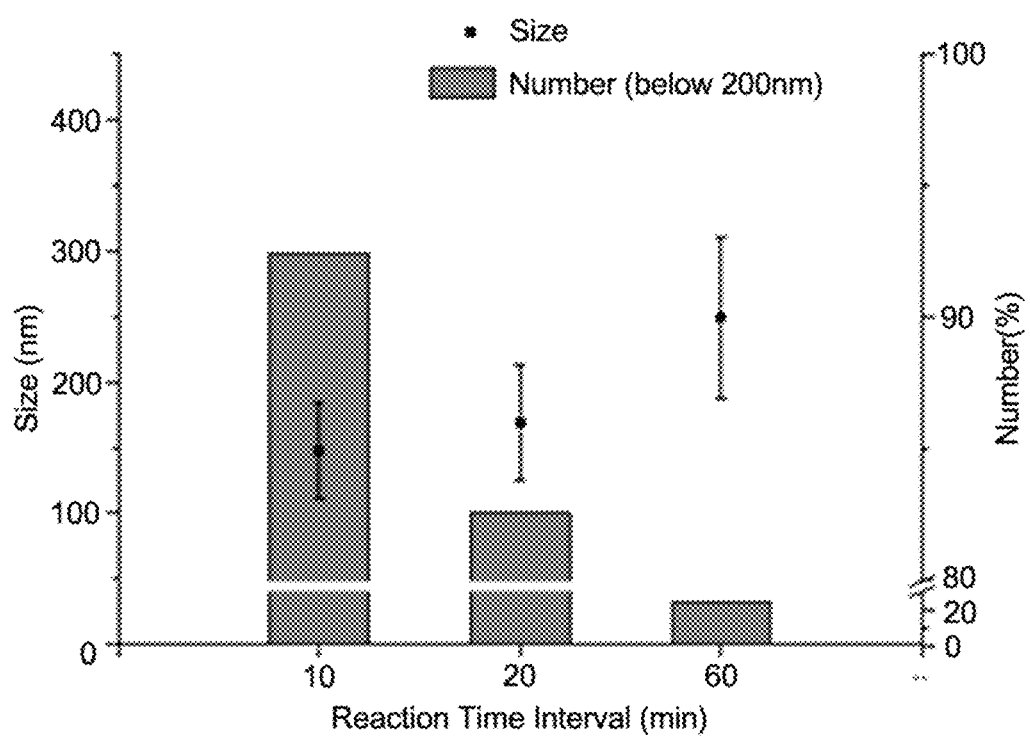
FIG. 6 shows the particle size and size distribution of DNA-RNA hybrid particles for different RTI.

Measurement of the Particle Size and Size Distribution of DNA-RNA Hybrid Particles According to Change in RTI The hybrid particles prepared in Example 3 and Example 5-1) and 2) were measured by dynamic light scattering using a particle size analyzer WI30i, and the results are given in FIG. 6. With increasing RTI, the average size of the hybrid particles was estimated to increase while the amount of particles smaller than 20 nm in size decreased. These results are believed to be attributable to the tendency of particles to form a net structure rather than a spherical shape when RTI is extended.

EXAMPLE 7

Figure 7:
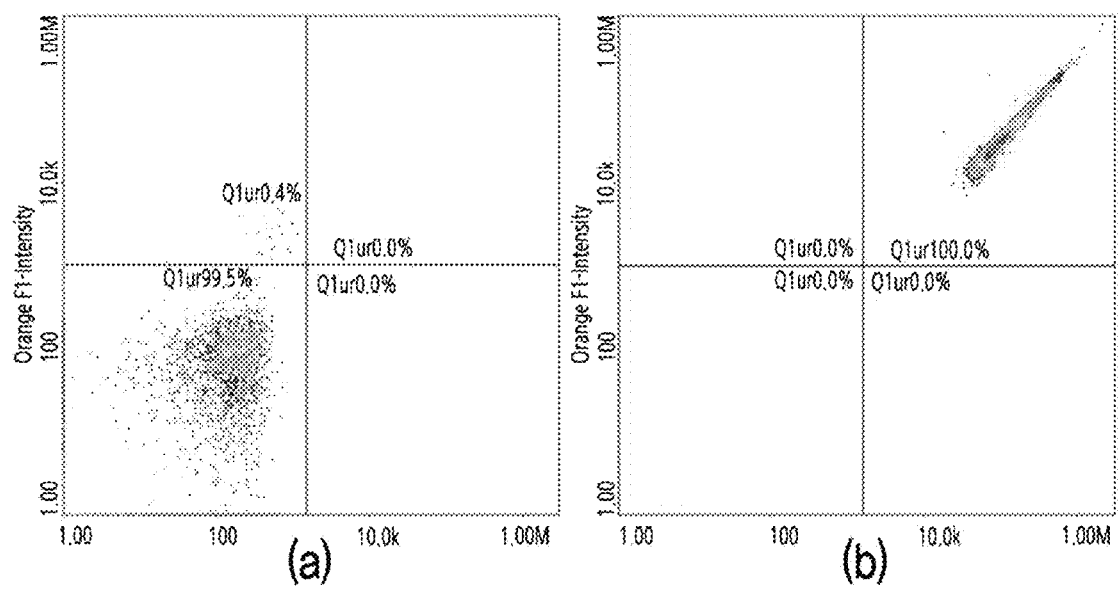
FIG. 7 shows the results of image cytometry of DNA-RNA hybrid particles for analyzing complementary binding therein.
Figure 8:
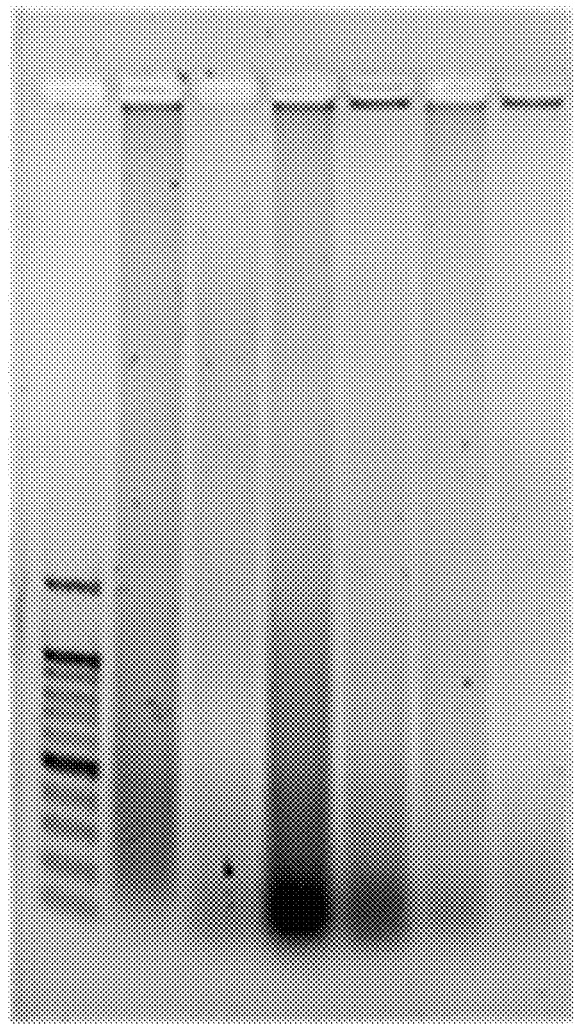
FIG. 8 shows the result of gel electrophoresis of DNA-RNA hybrid particles for analyzing complementary binding for different RTI.

Analysis for Complementary Binding Between DNA and RNA Strands in DNA-RNA Hybrid Particles 1) DNA-RNA hybrid particles were prepared according to the same procedure as described in Example 3, except that an rNTP mix containing Cy3-UTP and a dNTP mix containing Cy5-dCTP were used.
2) DNA-RNA hybrid particles, prepared in Example 3 and Example 7-1), were subjected to image cytometry. The results are shown in FIG. 7. Cy3-UTP, which emits orange fluorescence, was incorporated into RNA strands, while Cy5-dCTP, which emits intense red fluorescence, was incorporated into DNA strands. The image cytometry resulted in that, relative to the hybrid particles of Example 3 not labeled with Cy3 and Cy5 (FIG. 7(a)), the fluorescent-labeled hybrid particles (Example 7-1)) produced two intensive fluorescence emissions (FIG. 7(b)), indicating that the hybrid particles of the present invention are composed of DNA and RNA molecules.
3) DNA-RNA hybrid particles, prepared in Example 3 and Example 5-1) and 2), were incubated with RNase H (2,000 U/ml) for 24 hrs to degrade the complementary base pairing between DNA and RNA strands, and were then analyzed on gel electrophoresis. The results are shown in FIG. 8, in which the leftmost lane is lane 1 while the rightmost lane is lane 7 (lane 1, 100 bp ladder; lane 2 (Example 3), lane 4 (Example 5-1)) and lane 6 (Example 5-2)), samples were incubated without RNase H; lane 3 (Example 3), lane 5 (Example 5-1)) and lane 7 (Example 5-2)), samples were incubated with RNase H). DNA-RNA hybrid particles were found to be completely digested (lane 3 compared to lane 2) when generated at an RTI of 10 min (Example 3), whereas, when prepared at an RTI of 20 min (Example 5-1)) or 60 min (Example 5-2)), they were rarely digested (lane 5 compared to lane 4, lane 7 compared to lane 6). These results indicate that the hybrid particles are composed of DNA and RNA, in which DNA and RNA strands become longer as the RTI is extended and thus form a fiber-like net structure rather than forming complementary binding between each other.

EXAMPLE 8

Evaluation of Resistance of DNA-RNA Hybrid Particles Against Nuclease Digestion

Figure 9:
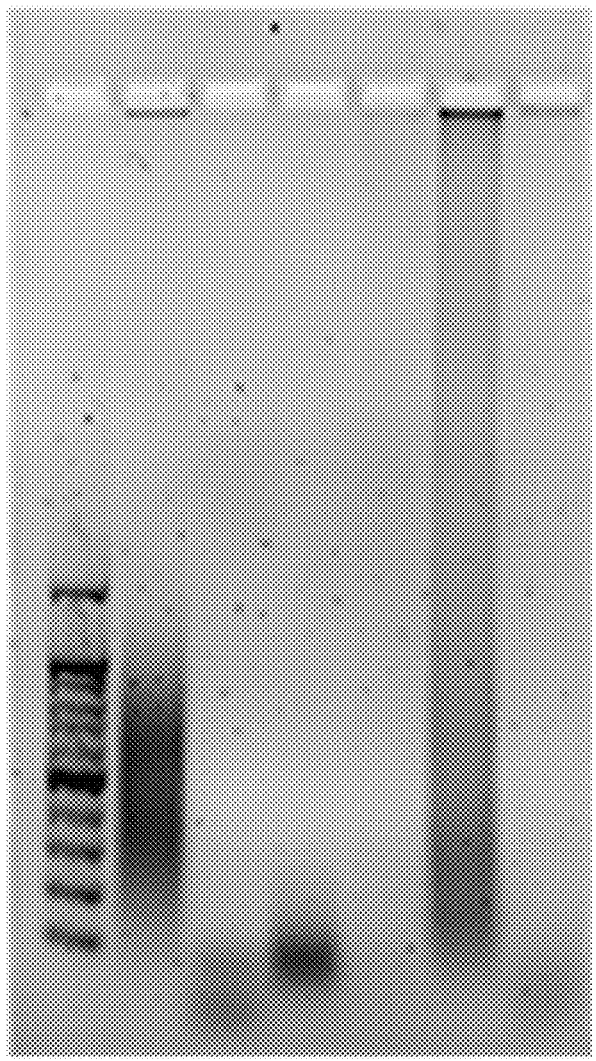
FIG. 9 shows the result of gel electrophoresis of DNA-RNA hybrid particles for analyzing resistance against nuclease digestion.

1) An RNA particle sample was generated by rolling circle transcription (RCT) with 3 pmol of the closed circular ssDNA for transcription, which was hybridized with the primer, T7 RNA Polymerase (500 unit), 20 μl of RNAPol Reaction Buffer (40 mM Tris-HCl, 6 mM MgCl$_2$, 10 mM DTT, 2 mM spermidine, pH 7.9 at 25° C.) and rNTP mix (200 nmol). The RCT reaction was performed in a total volume of 50 μl at 37° C. (RPAT) for 20 hrs (RTI).
2) A DNA particle sample was generated by rolling circle amplification (RCA) with 3 pmol of the closed circular ssDNA for amplification, which was hybridized with the primer, Phi29 DNA Polymerase (500 unit ₁ ₋), 20 μl of Reaction Buffer (400 mM Tris-HCl, 500 mM KCl, 100 mM MgCl$_2$, 50 mM (NH$_4$)$_2$SO$_4$, 40 mM DTT and dNTP mix (200 nmol). The RCA reaction was performed in a total volume of 50 μl at 30° C. (DPAT) for 20 hrs (RTI).
3) The DNA-RNA hybrid particles prepared in Example 3 and the RNA and DNA particle samples prepared in the above 1) and 2), respectively, were incubated with a nuclease for 5 hrs and then loaded into gel electrophoresis apparatus. The result is shown in FIG. 9, in which the leftmost lane is lane 1 and the rightmost lane is lane 7 (lane 1, 100 bp ladder; lane 2, the DNA sample was not treated with any nuclease; lane 3, the DNA sample was treated with DNase I; lane 4, the RNA sample was not treated with any nuclease; lane 5, the RNA sample was treated with RNases I and III; lane 6, the hybrid particle sample was not treated with any nuclease; lane 7, the hybrid particle sample was treated with DNase I and RNases I and III). Referring to FIG. 9, when particles were composed of only DNA (the DNA sample), they were completely degraded by DNase I (lane 3 compared to lane 2). Particles consisting of only RNA (the RNA sample) were also completely degraded by RNase I and III (lane 5 compared to lane 4). In contrast, when DNA and RNA strands were aggregated into nano-sized particles through complementary binding, they were degraded to some extent by nucleases but a relatively large quantity still remained intact (lane 7 compared to lane 6). This result demonstrated that the nano-sized hybrid particles have resistance against nuclease digestion.

EXAMPLE 9

Evaluation of Delivery Efficiency of DNA-RNA Hybrid Particles into Target Cells 1) DNA-RNA hybrid particles were prepared according to the same procedure as described in Example 3, except that the dNTP mix contained Cy5-dCTP (a red florescent dye).

2) DNA-RNA hybrid particles were prepared according to the same procedure as described in the above 1) of Example 9, except that the ssDNA strand for amplification contained a meaningless sequence of SEQ ID NO: 9 (CGAC-CACTAGGATTACAGCCACCTTCACC), which is unable to act as an aptamer, instead of the sequence complementary to a nucleolin (NCL)-aptamer sequence, which is represented by SEQ ID NO: 6 (CCACCACCACCACCACAAC-CACCACCACC).

3) ① MDA-MB-231 cells were seeded in a 96-well plate at a density of $7 \times 10^3$ cells/ml, ② and were allowed to completely adhere to the bottom of the wells for 24 hrs. ③ After the growth medium was discarded, the hybrid particles prepared in the above 1) of Example 9 were mixed with Opti-MEM at a 1:3 ratio and added to each well. ④ After the cells were incubated for 4 hrs, the medium was discarded and the cells were fixed with a fixative solution of 4% paraformaldehyde. ⑤ The fixative solution was removed 10 min later, and the cells were treated with an actin dye for 10 min so as to stain the cytoplasm. ⑥ After the actin dye solution was removed, a slide was treated with a mounting solution. ⑦ The slide was then overlaid with a cover glass and was subjected to confocal microscopy. The resulting confocal microscopic images are shown in FIG. 10(*b*), FIG. 11 and FIG. 12(*a*).

4) As a control, MDA-MB-231 cells were not treated with the hybrid particles prepared in the above 1) of Example 9, while the other conditions were kept the same as in the above 3). The result is shown in FIG. 10(*a*).

Figure 11:
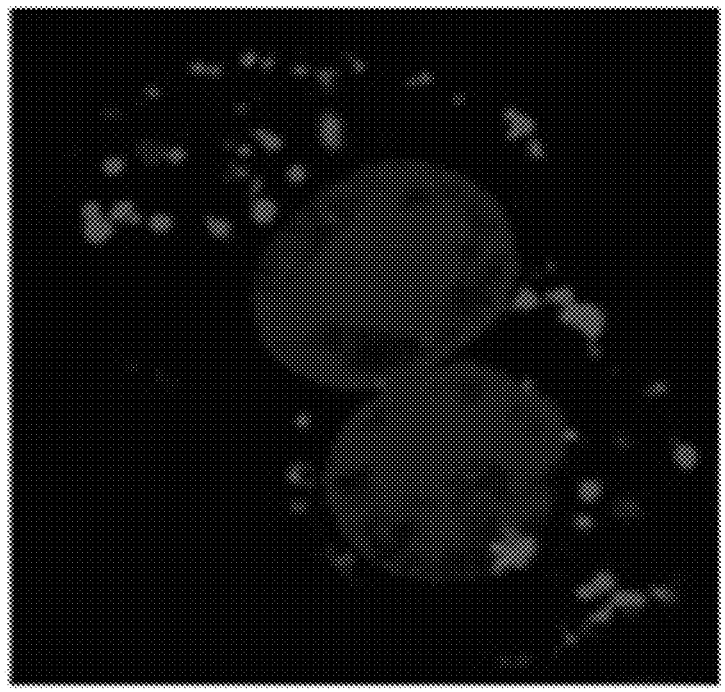
Figure 12:
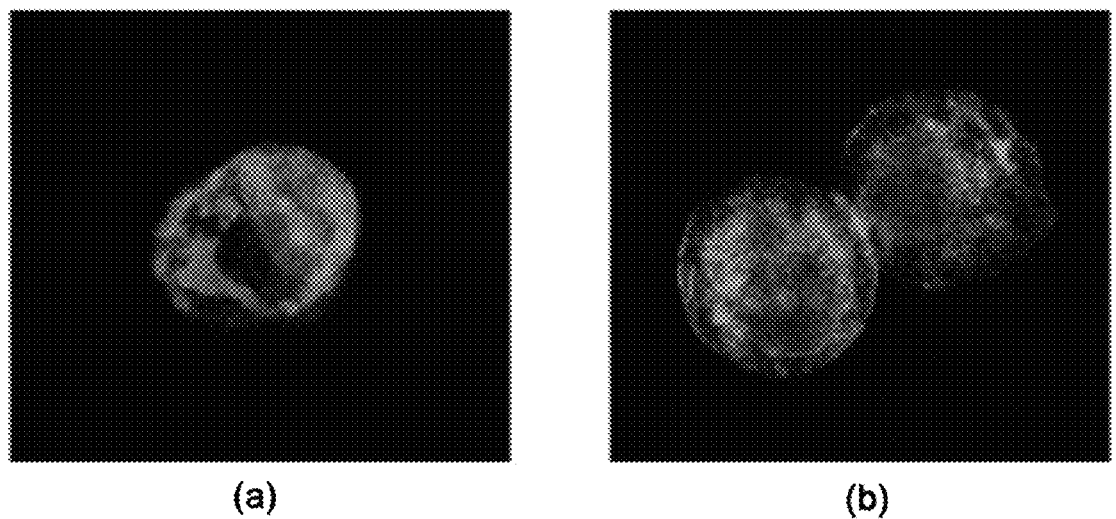

5) MDA-MB-231 cells were treated with the hybrid particles prepared in the above 2) of Example 9 instead of those prepared in the above 1) of Example 9, while other conditions were the same as in the above 3) of Example 9. The result is shown in FIG. 12(*b*). Relative to cells in FIG. 10, FIGS. 11 and 12 shows enlarged images of cells with sequentially increasing microscopic magnification.

Figure 10:
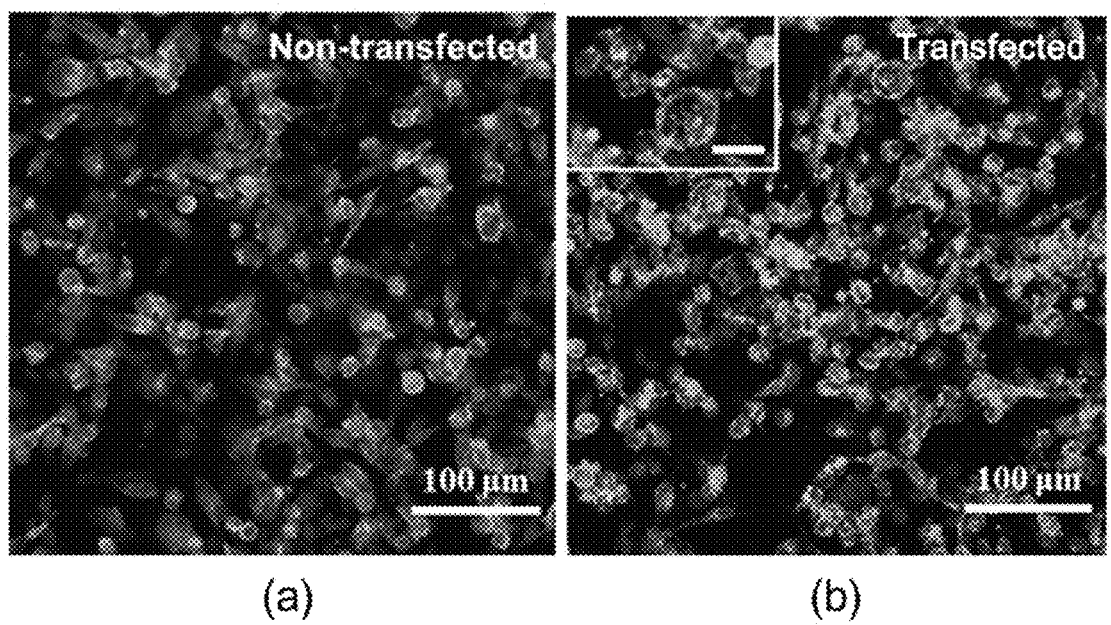
FIGS. 10 to 12 show confocal microscopic images of DNA-RNA hybrid particles for analyzing their intracellular delivery efficiency.

6) As compared with non-transfected cells (Example 9-4)), transfected cells (Example 9-3)) displayed red fluorescence in the cytoplasm (FIG. 10(*a*) vs FIG. 10(*b*)). As shown in FIG. 11, plenty of hybrid particles (red signal) were present in the cytoplasm and around the cell membrane (blue signal). As shown in FIG. 12(*a*), the hybrid particles (red) containing an NCL-aptamer sequence were localized in the cytoplasm (green, blue), whereas the hybrid particles containing the meaningless sequence were not present in the cytoplasm (FIG. 12(*b*)). Thus, the hybrid particles were found to be effectively delivered into cells because a plenty of the hybrid particles having an NCL-aptamer sequence were localized around the cell membrane and in the cytoplasm.

EXAMPLE 10

Cytotoxicity Assay for DNA-RNA Hybrid Particles

1) ① HeLa cells were seeded in a 96-well plate at a density of $7 \times 10^3$ cells/ml, ② and were allowed to completely adhere to the bottom of the wells for 24 hrs. ③ After the growth medium was discarded, the hybrid particles prepared in Example 3 were mixed with Opti-MEM to give final concentrations of 0, 0.04, 0.2, 1 and 5 fM, and were added to each well. ④ After 4 hrs of incubation, the medium was discarded, ⑤ and the cells were again fed with fresh growth medium and further incubated for 48 hrs. ⑥ After the growth medium was discarded, a stock solution of MTT (3-[4,5-dimethylthiazol-2-yl]-2,5-diphenyltetrazolium bromide) was added to each well, and the cells were incubated for 4 hrs. ⑦ Thereafter, a solvent was added to each well to solubilize the resulting formazan crystal. ⑧ The absorbance of this colored solution was measured at 570 nm, ⑨ and the resulting absorbance values were compared with that of control cells, which were not treated with the hybrid particles. The results are shown in FIG. 13.

Figure 13:
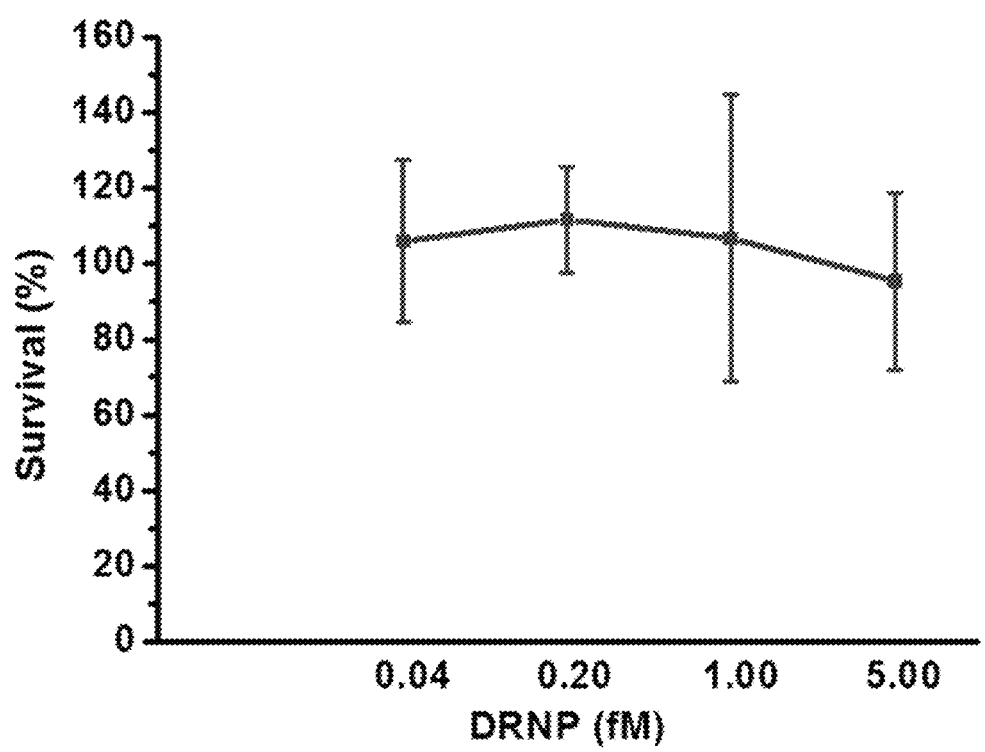
FIG. 13 shows the result of cell viability assay for evaluating the cytotoxicity of DNA-RNA hybrid particles.

2) As shown in FIG. 13, when cells were treated with increasing concentrations of the hybrid particles, they displayed a cell viability of more than 95%. These results indicate that the hybrid particles according to the present invention have very excellent in-vivo compatibility because they are composed of only DNA and RNA molecules.

EXAMPLE 11

Evaluation for RNA Interference by DNA-RNA Hybrid Particles

1) ① HeLa cells, into which a luciferase reporter gene was introduced, were seeded in a 96-well plate at a density of $7 \times 10^3$ cells/ml, ② and were allowed to completely adhere onto the bottom of the wells for 24 hrs. ③ After the growth medium was discarded, the hybrid particles prepared in Example 3 were mixed with Opti-MEM to give final concentrations of 0, 1, 2.5 and 5 fM, and were added to each well. ④ After 4 hrs of incubation, the medium was discarded, ⑤ and the cells were again fed with fresh growth medium and further incubated for 48 hrs. ⑥ Then, a stock solution of Dual-Glo luciferase reagent was added to each well. After 10 min, the luminescence was measured at 590 nm in a microplate reader. ⑦ After 48 hrs, a stock solution of Dual-Glo stop & Glo reagent was added to each well, and 10 min later, the luminescence was measured at 590 nm in a microplate reader. The resulting luminescence values were expressed relative to the control cells not treated with hybrid particles, and are shown in FIG. 14.

Figure 14:
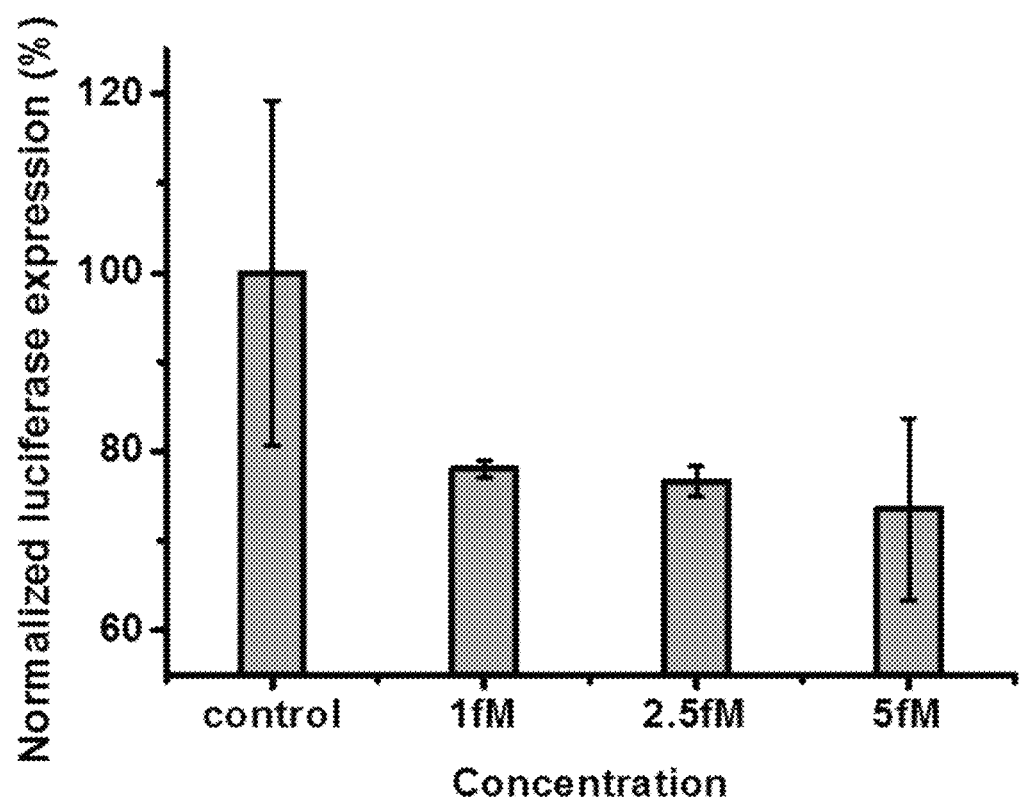
FIG. 14 shows the result of a luciferase reporter-based assay for monitoring RNA interference by DNA-RNA hybrid particles.

2) As shown in FIG. 14, as compared with the control, luciferase expression was reduced in cells treated with the hybrid particles, and this reduction was observed in a concentration-dependent manner. These results indicate that the long RNA strands of the hybrid particles are cleaved into siRNA fragments by the endoribonuclease dicer, and that these siRNA fragments induce RNA interference (RNAi) inside cells.

Although a variety of embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of manufacturing DNA-RNA hybrid particles, comprising:
    generating a circular DNA template for transcription by allowing complementary base pairing between a primer and a single-stranded DNA (ssDNA) for transcription containing a nucleotide sequence complementary to a specific siRNA sequence;
    generating a circular DNA template for amplification by allowing complementary base pairing between a primer and a single-stranded DNA (ssDNA) for amplification containing a nucleotide sequence complementary to a specific aptamer sequence; and
    performing a stepwise dual enzymatic reaction, by which the circular DNA template for transcription is transcribed using an RNA polymerase to generate an RNA strand containing the siRNA sequence, the circular DNA template for amplification is amplified using a DNA polymerase to generate a DNA strand containing the aptamer sequence, and partial complementary base pairing is allowed to form particles between the RNA strand containing the siRNA sequence and the DNA strand containing the aptamer sequence.

2. The method of claim 1, wherein the RNA strand containing the siRNA sequence is generated by rolling circle transcription (RCT), and the DNA strand containing the aptamer sequence is generated by rolling circle amplification (RCA).

3. The method of claim 1, wherein the stepwise dual enzymatic reaction is carried out as a first reaction over a first predetermined time at first activation temperature for RNA and as a second reaction over a second predetermined time at a second activation temperature for DNA polymerases and repeating the first reaction and the second reaction for a third predetermined time.

4. The method of claim 1, wherein the stepwise dual enzymatic reaction comprises:
    (1) mixing the DNA template for transcription with the RNA polymerase in a container and maintaining a first reaction at a first activation temperature for RNA polymerase for a first predetermined reaction time;
    (2) mixing the DNA template for amplification with the DNA polymerase in an additional container and maintaining a second reaction at a second activation temperature for DNA polymerase for a second predetermined reaction time; and
    (3) mixing the resulting reaction in the container with the resulting reaction in the additional container and maintaining repeating a first reaction and the second reaction for a third predetermined time.

5. The method of claim 3, wherein the first, the second, and the third predetermined time are controlled so as to form particles in a predetermined size and shape.

6. The method of claim 1, wherein the generating the circular DNA template for amplification comprises:
    hybridizing a primer and a single-stranded DNA (ssDNA) for amplification containing a nucleotide sequence complementary to a specific aptamer sequence through complementary base pairing; and
    ligating a nick in the resulting circular ssDNA with a ligase.

7. The method of claim 1, wherein the generating the circular DNA template for amplification comprises:
    hybridizing a primer and a single-stranded DNA (ssDNA) for amplification containing a nucleotide sequence complementary to a specific aptamer sequence through complementary base pairing; and ligating a nick in the resulting circular ssDNA with a ligase.

* * * * *

```
                           SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: region of ssDNA for binding primer

<400> SEQUENCE: 1
atagtgagtc gtattaacgt a                                            21

<210> SEQ ID NO 2
<211> LENGTH: 57
<212> TYPE: DNA
<213> ORGANISM: Artificial Sequence
<220> FEATURE:
<223> OTHER INFORMATION: region of ssDNA for siRNA generation

<400> SEQUENCE: 2
ccaacaactt acgctgagta cttcgattac ttgaatcgaa gtactcagcg taagttt     57

<210> SEQ ID NO 3
<211> LENGTH: 14
<212> TYPE: DNA
<213> ORGANISM: Artificial Sequence
<220> FEATURE:
<223> OTHER INFORMATION: region of ssDNA for binding primer

<400> SEQUENCE: 3
agaggcatat ccct                                                    14

<210> SEQ ID NO 4
<211> LENGTH: 22
<212> TYPE: DNA
<213> ORGANISM: Artificial Sequence
<220> FEATURE:
<223> OTHER INFORMATION: primer for circular DNA generation

<400> SEQUENCE: 4
taatacgact cactataggg at                                           22

<210> SEQ ID NO 5
<211> LENGTH: 26
<212> TYPE: DNA
<213> ORGANISM: Artificial Sequence
<220> FEATURE:
<223> OTHER INFORMATION: region of ssDNA for binding primer

<400> SEQUENCE: 5
agggatatgc ctctaataaa tattaa                                       26

<210> SEQ ID NO 6
<211> LENGTH: 29
<212> TYPE: DNA
<213> ORGANISM: Artificial Sequence
<220> FEATURE:
<223> OTHER INFORMATION: region of ssDNA for aptamer generation

<400> SEQUENCE: 6
ccaccaccac caccacaacc accaccacc                                    29
```

```
<210> SEQ ID NO 7
<211> LENGTH: 37
<212> TYPE: DNA
<213> ORGANISM: Artificial Sequence
<220> FEATURE:
<223> OTHER INFORMATION: region of ssDNA for binding primer

<400> SEQUENCE: 7
aataataaga agttggtacg ttaatacgac tcactat                              37

<210> SEQ ID NO 8
<211> LENGTH: 22
<212> TYPE: DNA
<213> ORGANISM: Artificial Sequence
<220> FEATURE:
<223> OTHER INFORMATION: primer for circular DNA generation

<400> SEQUENCE: 8
ttagaggcat atccctatag tg                                              22

<210> SEQ ID NO 9
<211> LENGTH: 29
<212> TYPE: DNA
<213> ORGANISM: Artificial Sequence
<220> FEATURE:
<223> OTHER INFORMATION: control region of ssDNA for comparing with
      aptamer

<400> SEQUENCE: 9
cgaccactag gattacagcc accttcacc                                       29
```